United States Patent [19]

Clarke et al.

[11] Patent Number: 5,723,623
[45] Date of Patent: Mar. 3, 1998

[54] METHOD OF TRANSFORMING PYRAZOLE COMPOUNDS

[75] Inventors: David Clarke, Watford; Hamish McNab, Edinburgh; Richard W. Mares, Penwortham, all of United Kingdom

[73] Assignee: Eastman Kodak Company, Rochester, N.Y.

[21] Appl. No.: 732,732

[22] Filed: Oct. 18, 1996

[30] Foreign Application Priority Data

Oct. 31, 1995 [GB] United Kingdom ............ 9522251

[51] Int. Cl.$^6$ ............................................. C07D 487/04
[52] U.S. Cl. ............................... 548/262.4; 548/371.4
[58] Field of Search ............................... 548/262.4

[56] References Cited

U.S. PATENT DOCUMENTS 5,510,492  4/1996  Tang et al. ..................... 548/262.4

Primary Examiner—Robert W. Ramsuer
Attorney, Agent, or Firm—Arthur E. Kluegel

[57] ABSTRACT

The invention provides a method of transforming a pyrazole compound, comprising cyclizing a 1,5-diaminopyrazole compound having the structure:

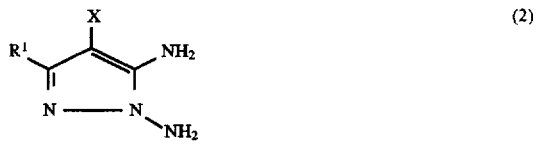

(2)

wherein $R^1$ is a substituent group; and X is hydrogen, an acyl group, or a heterogroup;
in an alkaline solution with carbon disulphide to produce a pyrazolotriazole thione compound having formula (3).

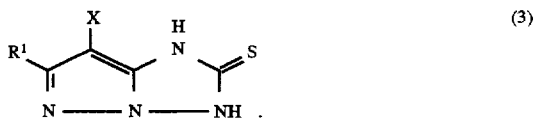

(3)

10 Claims, No Drawings

METHOD OF TRANSFORMING PYRAZOLE COMPOUNDS

FIELD OF THE INVENTION

The invention relates to the transformation of pyrazole compounds. More particularly, it relates to the synthesis of 1H-pyrazolo[1,5-b][1,2,4]-triazoles useful in the color photographic process as magenta or cyan dye-forming agents.

BACKGROUND OF THE INVENTION

The synthesis and photographic properties of 1H-pyrazolo[1,5-b][1,2,4]-triazoles have been extensively covered in the patent literature. For example, EP-A-0 119 860 describes a wide range of synthetic approaches to the ring system which can then be utilized as magenta couplers.

The synthetic route most frequently described is based on the conversion of a 3(5)-aminopyrazole to its amidoxime derivative. Subsequently, the amidoxime, or more frequently its o-tosylate derivative, is thermally cyclized to the desired 1H-pyrazolo[1,5-b][1,2,4]-triazole as shown in Scheme 1 below.

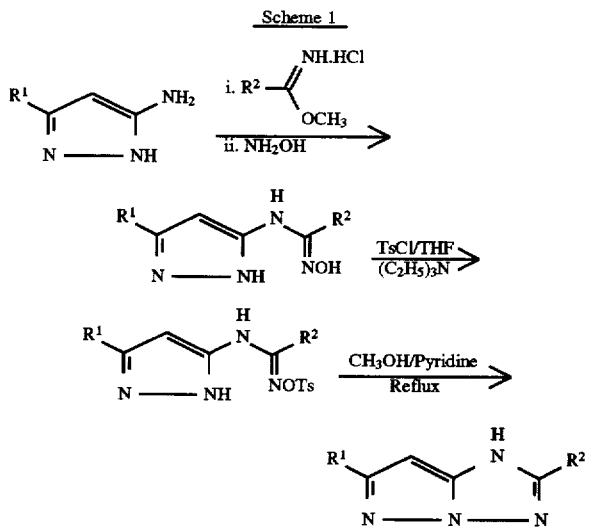

In the above scheme, Ts represents tosyl.

Although this route enables a wide variety in substituent $R^1$, it is limiting for $R^2$, which in practice is largely restricted to alkyl or aryl.

It is a problem to be solved to provide a convenient method for transforming pyrazole compounds which enables a sulfur linkage to the compound.

SUMMARY OF THE INVENTION

The invention provides a method of transforming a pyrazole compound, comprising cyclizing a 1,5-diaminopyrazole compound having the structure:

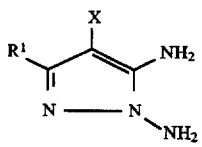   (2)

wherein $R^1$ is a substituent group; and X is hydrogen, an acyl group, or a heterogroup;
in an alkaline solution with carbon disulphide to produce a pyrazolotriazole thione compound having formula (3).

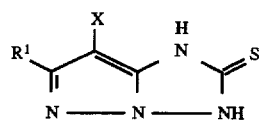   (3)

The method of the invention provides a convenient method for transforming pyrazole compounds which enables a sulfur linkage to the compound.

DETAILED DESCRIPTION OF THE INVENTION $R^1$ is a substituent group (as described hereafter), and in the case of a coupler compound destined for photographic use, may suitably be a coupler-modifying functional substituent group.

$R^1$ may, for example, be a solubilising group, ballasting group or dye hue-modifying group. $R^1$ is preferably a group selected from alkyl; alkoxy; alkylthio; aryl; aryloxy; arylthio; heterocyclyl; acyl e.g. alkyl- or aryl-carbonyl; acylamino; carboxylic acid or ester e.g. alkoxy- or aryloxy-carbonyl; primary, secondary or tertiary amino e.g. alkyl- or aryl-amino; primary or secondary amido e.g. alkyl- or aryl-amido; sulfonamido e.g. alkyl- or aryl-sulfonamido; sulfonyl e.g. alkyl- or aryl-sulfonyl; sulfonyloxy e.g. alkyl- or aryl-sulfonyloxy; sulfinyl e.g. alkyl- or aryl-sulfinyl; sulfamoyl e.g. alkyl- or aryl-sulfamoyl; carbamoyl e.g. alkyl- or aryl-carbamoyl; and cyano groups.

Particularly preferred $R^1$ groups include alkyl and alkoxy groups having from 1 to 18, preferably 1 to 4, carbon atoms; alkylsulfonyl groups having from 1 to 18, preferably 1 to 4, carbon atoms; phenyl groups; phenyloxy groups; and a cyano group $R^1$ is most preferably a t-alkyl group having from 4 to 10 carbon atoms e.g. t-butyl, t-octyl, adamantyl, or t-pentyl.

$R^2$ is a group selected from alkyl and aryl groups. The alkyl and aryl groups may be substituted with one or more of the $R^1$ groups defined above or other substituents known in the art such as hydroxy, halo and nitro groups. Preferred $R^2$ groups include alkyl groups having from 1 to 18 carbon atoms; phenyl groups, possibly substituted with one or more nitro groups e.g. 2- or 4-nitrophenyl.

X is hydrogen, acyl, or a heterogroup (a halogen or a group connected by a P, S, O, or N atom such as a coupling off group known to those skilled in the photographic art). Examples include halogen, particularly chlorine, bromine, or fluorine, alkoxy, aryloxy, heterocyclyl, such as hydantoin and pyrazolo groups, heterocyclyloxy, heterocyclylimido, heterocyclylthio, sulfonyloxy, acyloxy, carbonamido, imido, acyl, thiocyano, alkylthio, arylthio, sulfonamido, phosphonyloxy and arylazo.

Examples of specific coupling-off groups are —Cl, —F, —Br, —SCN, —OCH$_3$, —OC$_6$H$_5$, —OCH$_2$C(=O)NHCH$_2$CH$_2$OH, —OCH$_2$C(=O)NHCH$_2$CH$_2$OCH$_3$, —OCH$_2$C(=O)NHCH$_2$CH$_2$OC(=O)OCH$_3$, —NHSO$_2$CH$_3$, —OC(=O)C$_6$H$_5$, —NHC(=O)C$_6$H$_5$, —OSO$_2$CH$_3$, —P(=O)(OC$_2$H$_5$)$_2$, —S(CH$_2$)$_2$CO$_2$H,

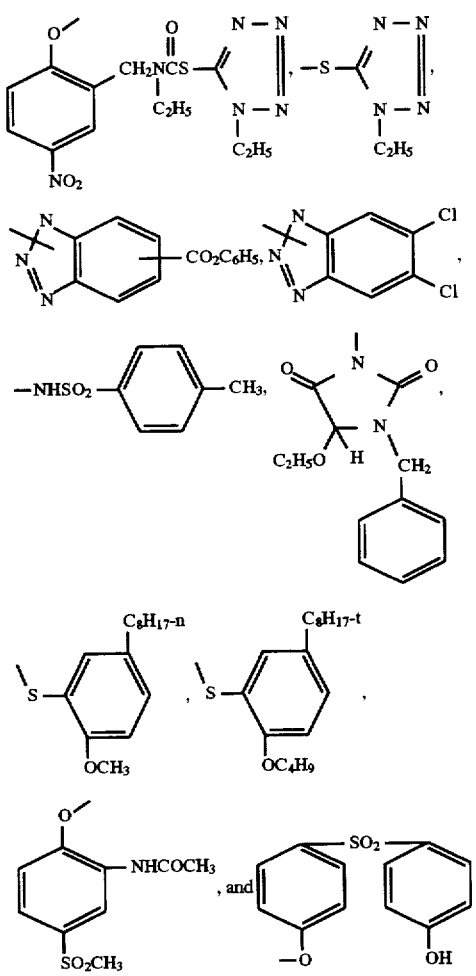

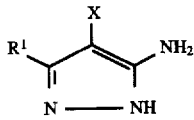

Preferably, X is H or halogen, and more preferably, H or Cl.

In addition to the cyclizing method of the invention, the pyrazole transformation method may involve additional preceding and succeeding steps. When all of the succeeding steps are employed, the invention provides a method of preparing a 1H-pyrazolo[1,5-b][1,2,4]-triazolecompound.

An optional preceding step is one comprising the step of N-aminating an aminopyrazole compound having the structure

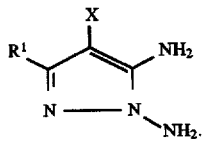  (1)

wherein

R¹ is a substituent group; and,

X is hydrogen or a heterogroup;

in alkaline solution using an aminating agent to produce a 1,5-diaminopyrazole having the structure:

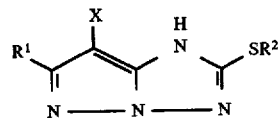  (2)

A succeeding step to the formation of compound (3) comprises alkylating or arylating the pyrazolotriazole thione in alkaline solution with an alkylating or arylating agent to produce a pyrazolotriazole compound having the structure:

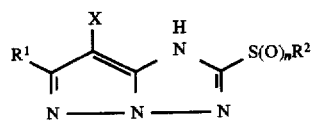

wherein R² is an alkyl or aryl group.

If desired, the method includes the further subsequent step of oxidizing the alkylthio or arylthio group of coupler (4) to the sulphoxide or sulphone to produce a compound having the structure

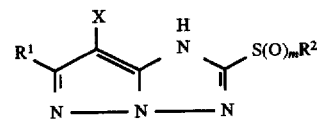  (5)

wherein n is 1 or 2.

The invention enables the formation of a 1H-pyrazolo[1,5-b][1,2,4]-triazole photographic coupler having the structure

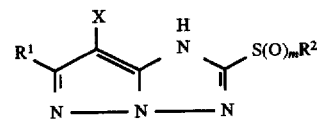  (6)

wherein

R¹, R² and X are as defined above, and m is 0, 1 or 2.

Unless otherwise specifically stated, substituent groups which may be substituted on molecules herein include any groups, whether substituted or unsubstituted, which do not destroy properties necessary for photographic utility or other ultimate use of the compound. When the term "group" is applied to the identification of a substituent containing a substitutable hydrogen, it is intended to encompass not only the substituent's unsubstituted form, but also its form further substituted with any group or groups as herein mentioned. Suitably, the group may be halogen or may be bonded to the remainder of the molecule by an atom of carbon, silicon, oxygen, nitrogen, phosphorous, or sulfur. The substituent may be, for example, halogen, such as chlorine, bromine or fluorine; nitro; hydroxyl; cyano; carboxyl; or groups which may be further substituted, such as alkyl, including straight or branched chain alkyl, such as methyl, trifluoromethyl, ethyl, t-butyl, 3-(2,4-di-t-pentylphenoxy) propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy)ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentylphenoxy)acetamido, alpha-(2,4-di-t-pentylphenoxy)butyramido, alpha-(3-pentadecylphenoxy)

hexanamido, alpha-(4-hydroxy-3-t-butylphenoxy) tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl)carbonylamino, p-dodecylphenylcarbonylamino, p-toluylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-toluylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-toluylsulfonamido, p-dodecylbenzenesulfonamido, N-methyltetradecylsulfonamido, N,N-dipropylsulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-toluylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-toluylsulfinyl; thio, such as ethylthio, octylthio, benzylthio, tetradecylthio, 2-(2,4-di-t-pentylphenoxy) ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1 (N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy.

If desired, the substituents may themselves be further substituted one or more times with the described substituent groups. The particular substituents used may be selected by those skilled in the art to attain the desired photographic or other properties for a specific application and can include, for example, hydrophobic groups, solubilizing groups, blocking groups, releasing or releasable groups, etc. Generally, the above groups and substituents thereof may include those having up to 48 carbon atoms, typically 1 to 36 carbon atoms and usually less than 24 carbon atoms, but greater numbers are possible depending on the particular substituents selected.

Preferred reaction conditions for the method of the invention are as follows.

In forming compound (3), the molar ratio of carbon disulphide to 1,5-diaminopyrazole may be 1 to 5, preferably 1 to 2. Suitable solvents for the reaction include methanol and ethanol. Examples of compounds which may be used to render the solution alkaline include potassium hydroxide, sodium hydroxide and triethylamine. The reaction may be carried out at a temperature from 0° C. to 100° C., preferably from 25° C. to 80° C.

In forming compound (2), the molar ratio of aminating agent to aminopyrazole may be 1 to 5, preferably 2 to 3. The aminating agent may be represented by the following structure $H_2N—O—SO_2R$ wherein R represents hydroxy or an aryl group e.g. phenyl or tolyl.

Suitable solvents for the reaction include dimethylformamide and dimethylacetamide. Examples of compounds which may be used to render the solution alkaline include potassium hydroxide and sodium hydroxide. The reaction may be carried out at a temperature from −10° C. to 25° C.

In forming compound (4), the molar ratio of alkylating or arylating agent to the pyrazolotriazole thione may be 1 to 5, preferably 1 to 2. Suitable alkylating agents include alkyl halides e.g. $C_{1-18}$ alkyl iodide, bromide or chloride. Preferred alkylating agents include methyl iodide and n-butyl bromide. Suitable arylating agents include aryl halides e.g. aryl chloride and aryl fluoride. Preferred arylating agents include p-nitrophenylfluoride. Suitable solvents for the reaction include methanol, ethanol and dimethylformamide. Examples of compounds which may be used to render the solution alkaline include potassium hydroxide, sodium hydroxide and triethylamine. The reaction may be carried out at a temperature from 0° C. to 100° C., preferably from 25° C. to 80° C.

In forming compound (5), a peroxide oxidizing agent may be employed. Examples of suitable oxidizing agents include hydrogen peroxide and percarboxylic acids e.g. 3-chloroperbenzoic acid. Suitable solvents for the reaction include acetic acid, dichloromethane and trichloromethane. The reaction may be carried out at a temperature from 0° C. to 100° C., preferably from 0° C. to 25° C.

Where the compound of the invention is destined for use as a photographic coupler, it can be used in any of the ways and in any of the combinations in which couplers are used in the photographic art. Typically, the coupler is incorporated in a silver halide emulsion and the emulsion coated on a support to form part of a photographic element.

Alternatively, the coupler can be incorporated at a location adjacent to the silver halide emulsion where, during development, the coupler will be in reactive association with development products such as oxidized color developing agent. Thus, as used herein, the term "associated" signifies that the coupler is in the silver halide emulsion layer or in an adjacent location where, during processing, the coupler is capable of reacting with silver halide development products.

The photographic elements can be single color elements or multicolor elements. Multicolor elements contain dye image-forming units sensitive to each of the three primary regions of the spectrum. Each unit can comprise a single emulsion layer or multiple emulsion layers sensitive to a given region of the spectrum. The layers of the element, including the layers of the image-forming units, can be arranged in various orders as known in the art. In a alternative format, the emulsions sensitive to each of the three primary regions of the spectrum can be disposed as a single segmented layer.

A typical multicolor photographic element comprises a support bearing a cyan dye image-forming unit comprising at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler, at least one of the couplers in the element being a coupler of this invention. The element can contain additional layers, such as filter layers, interlayers, overcoat layers, subbing layers, and the like.

In the following discussion of suitable materials for use in photographic emulsions and elements, reference will be made to Research Disclosure, December 1989, Item No. 308119, available as described above which will be identified hereafter by the term "Research Disclosure." The contents of the Research Disclosure, including the patents and publications referenced therein, are incorporated herein by reference, and the Sections hereafter referred to are Sections of the Research Disclosure.

The silver halide emulsions can be either negative-working or positive-working. Suitable emulsions and their preparation as well as methods of chemical and spectral sensitization are described in Sections I through IV. Color materials and development modifiers are described in Sections V and XXI. Vehicles are described in Section IX, and various additives such as brighteners, antifoggants, stabilizers, light absorbing and scattering materials, hardeners, coating aids, plasticizers, lubricants and matting agents are described, for example, in Sections V, VI, VIII, X, XI, XII, and XVI. Manufacturing methods are described in Sections XIV and XV, other layers and supports in Sections XIII and XVII, processing methods and agents in Sections XIX and XX, and exposure alternatives in Section XVIII.

Preferred color developing agents are p-phenylenediamines. Especially preferred are:

4-amino N,N-diethylaniline hydrochloride, 4-amino-3-methyl-N,N-diethylaniline hydrochloride, 4-amino-3-methyl-N-ethyl-N-(b-(methanesulfonamido)ethyl)aniline sesquisulfate hydrate, 4-amino-3-methyl-N-ethyl-N-(b-hydroxyethyl)aniline sulfate, 4-amino-3-b-(methanesulfonamido)ethyl-N,N-diethylaniline hydrochloride and 4-amino-N-ethyl-N-(2-methoxyethyl)-m-toluidine di-p-toluene sulfonic acid.

With negative working silver halide a negative image can be formed. Optionally positive (or reversal) image can be formed.

The magenta coupler described herein may be used in combination with other types of magenta image couplers such as 3-acylamino- or 3-anilino-, 5-pyrazolones and heterocyclic couplers (e.g.) pyrazoloazoles) such as those described in EP 285,274; U.S. Pat. No. 4,540,654; EP 119,860, or with other 5-pyrazolone couplers containing different ballasts or coupling-off groups such as those described in U.S. Pat. No. 4,301,235; U.S. Pat. No. 4,853,319 and U.S. Pat. No. 4,351,897. The coupler may also be used in association with yellow or cyan colored couplers (e.g. to adjust levels of interlayer correction) and with masking couplers such as those described in EP 213,490; Japanese Published Application 58-172,647; U.S. Pat. No. 2,983,608; German Application DE 2,706,117C; U.K. Patent 1,530,272; Japanese Application A-113935; U.S. Pat. No. 4,070,191 and German Application DE 2,643,965. The masking couplers may be shifted or blocked.

Photographic elements can be exposed to actinic radiation, typically in the visible region of the spectrum, to form a latent image and then processed to form a visible dye image. Processing to form a visible dye image includes the step of contacting the element with a color developing agent to reduce developable silver halide and oxidize the color developing agent. Oxidized color developing agent in turn reacts with the coupler to yield a dye.

With negative-working silver halide, the processing step described above provides a negative image. The described elements can be processed in the known C-41 color process as described in, for example, the British Journal of Photography Annual of 1982, pages 209–211 and 1988, pages 191–198 or in known processes for processing color photographic papers, such as the known RA-4 process of Eastman Kodak Company. The described elements are optionally processed in the known color processes for processing color print papers, such as the processes described in the British Journal of Photography Annual of 1988, pages 198–199. To provide a positive (or reversal) image, the color development step can be preceded by development with a non-chromogenic developing agent to develop exposed silver halide, but not form dye, and then uniformly fogging the element to render unexposed silver halide, but not form dye, and then uniformly fogging the element to render unexposed silver halide developable. Alternatively, a direct positive emulsion can be employed to obtain a positive image.

Development is followed by the conventional steps of bleaching, fixing, or bleach-fixing, to remove silver or silver halide, washing, and drying.

The invention is further illustrated by way of example as follows.

EXAMPLE 1

The following sequence of reactions was carried out to synthesize the coupler having the structure (4) above wherein $R^1$ represents t-butyl, $R^2$ represents methyl and X represents hydrogen, from readily available 3-amino-5-t-butylpyrazole. In addition, the coupler was oxidatively coupled with 4-diethylamino-3-methylaniline hydrochloride (CD2 developer) to give a representative azamethine dye.

Preparation of Coupler

3-Amino-5-t-butylpyrazole (1.4 g, 10 mmole) was dissolved in dry dimethylformamide (DMF) (15 ml) and cooled to −10 C. Crushed potassium hydroxide (4.2 g) was added and the solution was left to stir for 20 min. Hydroxylamine-O-sulphonic acid (2.3 g, 20 mmole) was added cautiously in small portions.

The resulting mixture was allowed to warmup to room temperature and was left stirring for 2 h. The mixture was then filtered and the DMF removed under reduced pressure. The semi-solid residue was redissolved. On removal of solvent, an oily product was obtained which consisted of diamine and starting material. The reaction was forced to completion by redissolving the crude mixture in DMF and the whole sequence repeated. The product was distilled under vacuum in a Kugelrohr apparatus to give the diamine having the structure (2) above, wherein $R^1$ represents t-butyl and X represents hydrogen, as a pale yellow oil, 1.07 g (70%), b.p. 128°–129° C./0.1 mm Hg.

Found: M+ 154.1214. $C_7H_{14}N_4$ requires M+ 154.1218; δH 5.20(1H, s), 4.50(4H, br, s), and 1.19(9H, s).

(The 4-chloro-1,5-diaminopyrazole analog was similarly prepared in a yield of 61% from its monoamine precursor.)

The diaminopyrazole (0.6 g, 4 mmole) was dissolved in methanol (10 ml). Water (0.3 ml) was added followed by potassium hydroxide (0.27 g, 5 mmole) and carbon disulphide (2.5 ml). The mixture was refluxed for 3 h, then cooled and neutralized with 5% hydrochloric acid and poured into water. The mixture was extracted with ethyl acetate (2×25 ml) and dried over MgSO4. On removal of solvent in vacuo, the pyrazolotriazole thione having the structure (3) above, wherein $R^1$ represents t-butyl and X represents hydrogen, was obtained as a semi-solid. This was used without further purification.

The thione derivative was dissolved in methanol (10 ml) then iodomethane (0.22 ml, 4 mmole) added followed by potassium hydroxide (0.2 g, 4 mmole). The mixture was stirred at room temperature for 2 h, then partitioned between ethyl acetate and 5% hydrochloric acid. The organic layer was dried and solvent removed to give the crude pyrazolotriazole coupler which was purified by silica gel column chromatography in 60/80 petrol/ethyl acetate (50:50) to give the desired pyrazolotriazole coupler as a pale yellow solid 0.045 g (6% overall), mp.226°–227° C.

Found: C, 50.1; H, 6.6; N, 25.6%
$C_9H_{14}N_4S$ Requires: C, 50.0; H, 6.8; N, 25.9%
δH(DMSO-d6), 12.77(1h, br, s), 5.61(1H, s), 2.61(3H, s) and 1.26(9H,s).
m/z 210(M+, 81%).

Preparation Azamethine Dye

The above coupler (0.052 g, 0.25 mmol) was dissolved in a mixture of 5% aqueous sodium carbonate (5 ml) and methanol(5 ml). Kodak CD2 developer, 4-amino-3-methyl-N,N-diethylaniline hydrochloride (0.062 g, 0.29 mmol) was added followed by solid potassium persulphate (0.15 g, 0.55 mmol). An intense purple coloration formed immediately and after stirring for 1 h, the precipitate was filtered off and dried. The azamethine dye produced was obtained as a purple solid, 0.077 g (81%), mp. 133–134 C.

Found: M+ 384.2097; $C_{20}H_{28}N_6S$ requires 384.2096. m/z 384(M+, 100%).

The dye gave a visually attractive magenta color in ethyl acetate solution λmax546 nm and εmax58,400. The half-height bandwidth was 66 nm in the same solvent. In cyclohexane and methanol the corresponding λmax were 524 and 558 nm, respectively.

The entire contents of the various patent applications, patents and other publications referred to in this specification are incorporated herein by reference.

What is claimed is:

1. A method of transforming a pyrazole compound, comprising cyclizing a 1,5-diaminopyrazole compound having the structure:

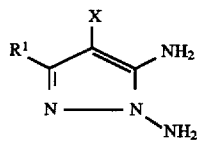

(2)

wherein $R^1$ is a substituent group; and X is hydrogen, an acyl group, or a heterogroup;
in an alkaline solution with carbon disulphide to produce a pyrazolotriazole thione compound having formula (3)

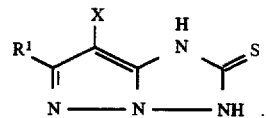

(3)

2. A method according to claim 1 wherein $R^1$ is selected from the group consisting of alkyl; alkoxy; alkylthio; aryl; aryloxy; arylthio; heterocyclyl; acyl; acylamino; carboxylic acid or ester; amino; amido; sulfonamido; sulfonyl; sulfonyloxy; sulfinyl; sulfamoyl; carbamoyl; and cyano groups.

3. A method according to claim 2 wherein $R^1$ is selected from the group consisting of alkyl and alkoxy groups having from 1 to 18 carbon atoms; alkylsulfonyl groups having from 1 to 18, carbon atoms; phenyl groups; phenyloxy groups; and a cyano group.

4. A method according to claim 3 wherein $R^1$ is a group selected from tertiary alkyl groups having from 4 to 10 carbon atoms.

5. A method according to claim 1 wherein X is selected from the group consisting of hydrogen, halogen, alkoxy, aryloxy, heterocyclyl, heterocyclyloxy, heterocyclylimido, heterocyclylthio, sulfonyloxy, acyloxy, carbonamido, imido, acyl, thiocyano, alkylthio, arylthio, sulfonamido, phosphonyloxy and arylazo groups.

6. The method of claim 1 additionally comprising preceding the cyclizing step of claim 1 with the step of N-aminating an aminopyrazole compound having the structure

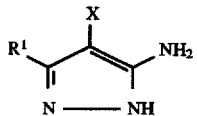

(1)

wherein $R^1$ and X are as defined in claim 1.

7. The method of claim 1 additionally comprising succeeding the cyclizing step of claim 1 with the step of alkylating or arylating compound (3) in alkaline solution with an alkylating or arylating agent to produce a pyrazolotriazole compound having formula (4):

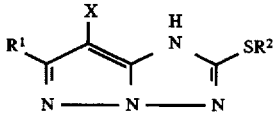

(4)

wherein $R^2$ is an alkyl or aryl group.

8. The method of claim 7 additionally comprising succeeding the alkylating or arylating step of claim 7 with the step of oxidizing the alkylthio or arylthio group of compound (4) to the sulphoxide or sulphone to produce a compound having formula (5) where n is 1 or 2

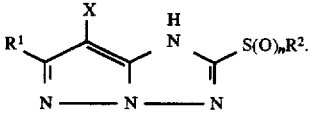

(5)

9. The method of claim 6 additionally comprising succeeding the cyclizing step with the step of alkylating or arylating compound (3) in alkaline solution with an alkylating or arylating agent to produce a pyrazolotriazole compound having formula (4):

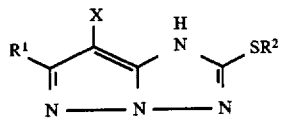
(4)
wherein $R^2$ is an alkyl or aryl group.
10. The method of claim 9 additionally comprising succeeding the alkylating or arylating step with the step of oxidizing the alkylthio or arylthio group of compound (4) to the sulphoxide or sulphone to produce a compound having formula (5) where n is 1 or 2
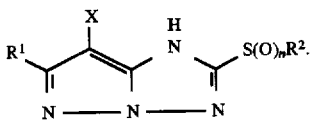
(5)
* * * * *